United States Patent [19]
Luca

[11] Patent Number: 5,516,646
[45] Date of Patent: *May 14, 1996

[54] METHOD OF DETECTING ABNORMAL EPITOPE EXPRESSION ON AN IMMUNOCAPTURED CONSTANT NUMBER OF PROTEIN MOLECULES

[76] Inventor: Nicolae Luca, 1210 E. Foster Rd., Unit B, Santa Maria, Calif. 93455

[*] Notice: The term of this patent shall not extend beyond the expiration date of Pat. No. 5,187,068.

[21] Appl. No.: 271,564

[22] Filed: Jul. 7, 1994

Related U.S. Application Data

[63] Continuation of Ser. No. 974,227, Nov. 10, 1992, abandoned, which is a continuation of Ser. No. 366,752, Jun. 9, 1989, Pat. No. 5,187,068.

[51] Int. Cl.$^6$ .................................................. G01N 33/53
[52] U.S. Cl. ................... 435/7.92; 435/7.1; 435/7.94; 436/518; 436/528; 436/531; 436/824
[58] Field of Search ................... 435/7.1, 7.92, 435/7.94, 11; 436/518, 528, 531, 824, 8

[56] References Cited

U.S. PATENT DOCUMENTS 4,703,017  10/1987  Campbell et al. ............ 436/501
5,187,068   2/1993  Luca ............................. 435/7.92

OTHER PUBLICATIONS

Linscott's Directory of Immunological and Biological Reagents, Fifth ed. 1988–1989, pp. 1–29, 31, 33–35,37–45, 53, 65,67,69,70 and 75.

American Diagnostics, Inc. Apr. 1991 Product List–Innovative Product for Research on and the Diagnosis of Clotting and Bleeding Disordes, pp. 10,12.

C. Birmingham (editor), Chemicon Communications, New Monoclonal Antibodies to Dystrophin (Spring 1992 pp. 2–3.

*Primary Examiner*—Carol A. Spiegel
*Attorney, Agent, or Firm*—Herbert Dubno; Jonathan Myers

[57] ABSTRACT

A method is disclosed for detecting abnormal epitope expression of protein molecules by immunocapturing a constant number of protein molecules from a test and a reference sample using a limited amount of capturing antibodies, saturating them with its corresponding protein from the test and reference samples to provide a constant, known amount of the immobilized protein for comparison, labelling an epitope on the immobilized protein by means of a labelled probing antibody specifically reactive with the epitope and correlating any difference in labelling between the test and the reference sample to the absence or modification of the epitope in the protein of the test sample.

4 Claims, 4 Drawing Sheets

METHOD OF DETECTING ABNORMAL EPITOPE EXPRESSION ON AN IMMUNOCAPTURED CONSTANT NUMBER OF PROTEIN MOLECULES

CROSS REFERENCE TO RELATED APPLICATIONS

This application is a continuation of Ser. No. 07/974,227, filed Nov. 10, 1992, now abandoned, which is a continuation of Ser. No. 07/366,752 filed on 9 Jun. 1989, now U.S. Pat. No. 5,187,068.

FIELD OF THE INVENTION

The invention relates to methods for detecting and measuring lipoproteins and particularly to determinations of corresponding lipid and apolipoprotein components carried out on intact lipoprotein species, in both a static and dynamic fashion.

BACKGROUND OF THE INVENTION

The initial Framingham epidemiological study established an indisputable link between lipids and coronary artery disease (CAD), and since the time of that initial study medical research efforts have advanced the understanding of lipid metabolism as well as the mechanisms of atherogenic processes which underlie CAD. There has been a corresponding effort to develop appropriate diagnostic tests which can identify individuals at risk for the disease and detect the disease in an early stage in order to provide effective preventive diet and drug therapy.

All lipoprotein classes are similar in that they have a hydrophobic core of non-polar lipids comprising triglycerides and cholesterol esters. They are coated, with phospholipids and cholesterol, in which specific proteins, the apolipoproteins, are embedded.

Lipoproteins are classified on the basis of their hydrated density. Accordingly, they are separated on ultracentrifugation into large, low density chylomicrons (<1.006 gm/mL;>100 nm), very low density lipoproteins (VLDL, d<1.006 gm/mL; 30–90 nm), intermediate density lipoproteins (IDL, d=1.006–1.019 gm/mL), low density lipoproteins (LDL, d=1.025–1.063 gm/mL; about 20 nm), and high density lipoproteins (HDL, d=1.063–1.21 gm/mL; about 8–12 nm).

The lipoprotein classes can also be identified by means of their associated apolipoproteins. Fourteen major human plasma apolipoproteins have been identified and their associations with lipoproteins characterized. The two major apolipoprotein on HDL are apo A-I and apo A-II. Chylomicrons are associated with apo $B_{48}$, and apo $B_{100}$ is the predominate apolipoprotein on VLDL and LDL. The apo C proteins are associated with all lipoproteins except LDL. Apoprotein E is a constituent of chylomicrons, VLDL, and HDL. Other Apolipoproteins, such as Lp(a), apo D and apo F are present in low concentrations. Their significance is poorly understood.

The function of the lipoproteins in lipid metabolism is primarily one of transport, but is nonetheless quite complex. Metabolism pathways comprise an exogenous system, wherein the lipoproteins transport triglycerides and cholesterol esters as well as other dietary lipids out of the intestine, and an endogenous system, wherein they transport corresponding hepatic lipids. The apolipoproteins on lipoproteins, by interacting with enzymes and cell surface receptors, direct lipoprotein lipids to an appropriate site of metabolism.

Since the defect in metabolism leading to atherosclerosis may be multifactorial, it is difficult to select the preferred marker or combination of markers to identify those patients who have an increased risk for premature cardiovascular disease. As the understanding of lipid metabolism has undergone rapid evolution, so have the clinical tests used to evaluate and predict CAD. Among the diagnostic ratios in present use are total cholesterol/HDL cholesterol, LDL cholesterol/HDL cholesterol, VLDL cholesterol/triglyceride, cholesterol/triglyceride, LDL cholesterol/Apo B, and HDL cholesterol/Apo $A_1$. Currently Apo $A_1$/ApoB is considered the best predictive ratio, and Lp(a), a cholesterol rich lipoprotein with pre-β mobility, the best independent risk marker.

One criticism of all these determinations is that they do not measure intact functional lipoproteins, but extracted or separated components. This may be particularly disadvantageous in the case of the apolipoprotein measurements. Studies show that immunological determinations of apolipoprotein vary with the conformation of the proteins, whether native or denatured, and also that their immunological reactivity is affected by lipid association, with greater numbers of epitopes being unmasked or expressed and available for antibody binding as lipid is lipolysed away. In the process of apolipoprotein isolation, lipoprotein lipid moiety is lost either inadvertently in the process of centrifugation, or purposefully, when lipases or detergents are used in separations, or preliminary to apolipoprotein quantitation. It is estimated that 35% of plasma Apo $A_1$ is lost upon prolonged centrifugation (Kunitake et al., J. Lipid Research 23:936-40 (1982)). As a result, normal apolipoprotein values cover a broad range and individual determinations are poorly reproducible.

Certain current methodologies for quantification of cholesterol and triglycerides in human serum using either chemical or enzymatic methods use solvent extraction or enzymatic hydrolysis of the substrates, a step which destroys the normal "anatomy" of lipoprotein particles. Both triglyceride and cholesterol values are very crude indicators of lipid moiety from lipoprotein particles. For example, triglycerides are estimated in total serum, not in VLDL, LDL, and HDL fractions; the cholesterol is chemically quantitated only for total cholesterol and HDL cholesterol; and LDL cholesterol and VLDL cholesterol are only indirectly computed.

The estimation of HDL cholesterol in lipemic samples (particularly postprandial samples) is exposed to errors due to the inability to precipitate large particles of chylomicrons, VLDL and LDL of lower density with manganese and heparin. There are large interlaboratory variations for cholesterol as well as for triglycerides, and usually no correction is made for free cholesterol. Therefore, the cutting point at which to evaluate patients at risk is very imprecise and, as a result, they may be committed to long-term diet or treatment with drugs unnecessarily.

The chemical isolation of the lipid fraction is an artificial approach disrupting the normal anatomy of lipoprotein particles. Triglycerides and cholesterol in body fluids perform their function not as isolated lipid fractions, but incorporated and intermingled with each other in lipoprotein particles, the normal way these lipid fractions operate in normal conditions in the body fluids.

Until now we quantified cholesterol and triglycerides because these were the techniques available. Presently we are able to isolate apo $B_{100}$ and apo $A_1$-containing particles by capturing them with specific antibodies. On these isolated particles I suggest now the study of the lipid moieties, a more meaningful approach.

The same considerations are true for apolipoproteins which do not circulate in the blood as isolated molecules, but as a component of an intact lipoprotein particle. In fact, even the International Union of Immunological Societies (IUIS) recommended as a standard for apo $A_1$ and apo $B_{100}$, a lyophilized pool of serum which contains intact lipoprotein particles (apo $A_1$ and apo $B_{100}$-containing particles (Naito, H., Clinical Chemistry 34(8):B84–94 (1988). Currently, both lipid fractions and apolipoproteins are expressed in mass units (mg/dl). The use of absolute mass units or absolute immunoreactive mass units is not essential. It is difficult to express a function or phenomenon, such as the masking or unmasking of apolipoproteins epitopes by lipids in fast or after meals, in mass units. What is essential in these studies is the direction of a phenomenon which can be detected using the relative units in multiple samples in a dynamic approach before and after meals, during a day.

The evaluation of lipoprotein particles by quantitating the amount of lipids only (triglyceride and cholesterol) was considered in the past to be misleading (Avogaro, P. et al., Lancet I: 901-3 (1979); Maciejko, J. J. et al., New Engl. J. Med. 309:385–389 (1983); and Snideman et al. Proc. Natl. Acad. Sci. 77(1):604–608 (1980)). The apolipoprotein component of the lipoprotein was suggested as more stable, and hence more suitable for diagnostic purposes. This view of "stability" is contradicted by my invention because it ignores the fact that both lipid and apolipoprotein component are extremely variable due to their dynamic changes in a normal lipoprotein particle physiology. In fact, the very essence of their function implies continuous changes in lipid components or in lipid moiety concentrations and apolipoprotein epitope expression. Therefore, my approach, instead of rejecting or ignoring this important fact recognizes the variability of both components (lipid moiety and apolipoprotein) and develops a method of studying this variability of lipid and apolipoprotein components in a dynamic fashion in an intact lipoprotein particle.

Unlike currently performed absolute quantifications of isolated livid fractions, (cholesterol and triglyceride), the present invention quantifies the whole lipid moiety (cholesterol, cholesterol esters, triglycerides, and phospholipids), using the fluorescent probe, Nile Red. This fluorescent probe dissolves in all these lipid fractions and can thus document their presence and quantity.

There is a hypothesis today that triglycerides and cholesterol are both involved in arterial wall damage. My approach of global quantification of lipid moiety is able to simultaneously study these two critical fractions. The technique presented is also more simple than those presently in use, and avoids all the complicated steps of lipid fraction quantification and therefore avoids errors. As a consequence, the technique is more precise, and it offers more meaningful information as well.

In the future, as more specific markers for each individual fraction are found or synthesized, they can be used to study these specific lipid fractions in an intact lipoprotein particle using the same technique.

Another criticism of current methodology is that lipid determination and apolipoprotein studies are done almost exclusively on fasting samples. This practice ignores the dynamic process of lipid metabolism that occurs after a meal, and in which the consequences of metabolic defects in lipolysis and receptor uptake occur.

Studying fasting samples for lipid moiety or apolipoprotein component offers limited information, and mainly only about the endogenous pathway, reflecting hepatic VLDL synthesis. Humans are not in a continuous fast. They eat at least three times a day; therefore, our lipoproteins are most of the time in a postprandial state. As a result of fatty meals, the lipid component of lipoproteins is continually changing, and the direction of this change is meaningful for at least some known physiological processes: lipid absorption, lipid clearance by intravascular processing by LPL and LDL receptor, dependent or independent tissue uptake. Because the lipid moiety of lipoproteins is in a dynamic state, this generates a dynamic expression of surface epitopes on apolipoproteins by masking (nonexpression) or unmasking (expressing) the epitopes by the lipids (Schonfeld, G. et al., J. Clin. Invest. 64:1288–1297 (1979). It is obvious that dynamic evaluation of lipoprotein particles for these two parameters, the lipid moiety and expressed epitopes on apolipoproteins, is highly desirable. This will generate a multitude of information. The lipoprotein particle has the main function of carrying the fat from the intestines and from the liver to the cells and from the cells to the liver. A challenge with a fatty meal will "put the lipoprotein particles to work." A normal human eats every day approximately 1 gram of fat per kilogram body weight which represents approximately 25 to 35 grams of lipids at each meal. If the lipoprotein transport mechanism is loaded with a standard amount of 70 grams of lipids or 1 gram lipid per kilogram in just one single meal (which represents the approximately 24 hour lipid load for a normal person) this will represent a veritable "lipid stress test." A normal profile of this response as well as an abnormal one will soon emerge, indicating normality or pathology (Chisiu, N. C. Rev. Roum. Biochim. 12(1):75–80 (1975) and Luca, N. et al., Rev. Roum. Biochim. 15(2):123–128 (1978).

It is therefore an object of the invention to provide procedures for lipoprotein determinations which overcome these limitations and avoid artifactual results.

It is also an object of the invention to provide a test system which permits the identification of defects in the metabolism and transport of lipids by providing data on the dynamics of relationship between lipid moiety and expressed apolipoprotein epitopes in the various lipoprotein species.

SUMMARY OF THE INVENTION

Figure 1:
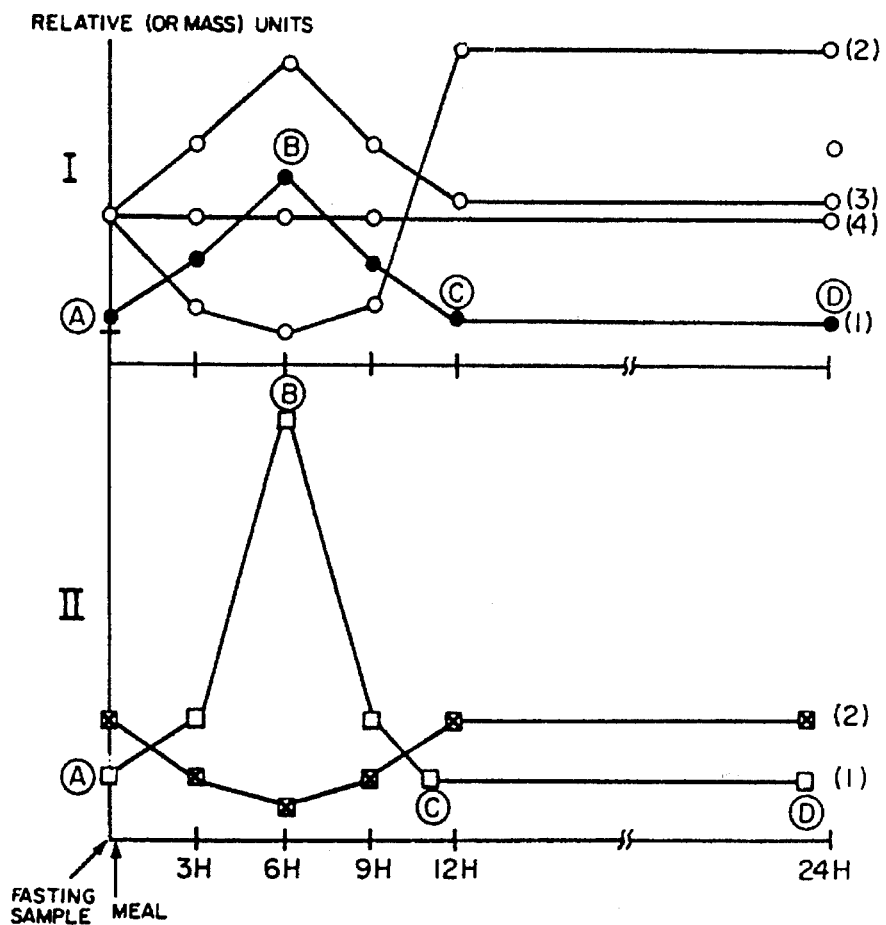
FIG. 1 is a series of graphs which plot the hypothetical dynamics of lipid moiety and expressed epitope immunoreactivity on apo $B_{100}$- and apo $A_1$-containing lipoproteins in normal subjects after a fatty meal against time over a 24 hour period.

According to one aspect of the invention, there is provided a method for determining the expressed epitopes of a protein in a sample from a specimen of bodily fluid, tissue or cells, comprising the steps of isolating a protein species from the sample and determining at least one expressed epitope on the protein by means of an agent specifically binding thereto. In a preferred embodiment, there is provided a method of determining the composition of intact lipoproteins in a sample from a specimen of bodily fluid, tissue, or cells, comprising the steps of isolating from the sample at least one intact lipoprotein species, which includes a selected apolipoprotein; determining at least one species of lipid in the intact lipoprotein species; and then determining at least one expressed epitope on at least one apolipoprotein in the intact lipoprotein species. In preferred embodiments, the species of protein or apolipoprotein is isolated by means of an agent specifically binding thereto. In another embodiment there is provided a method for determining the composition of intact lipoproteins in a sample from a specimen of bodily fluid, tissue, or cells, comprising the steps of isolating from the sample at least one intact lipoprotein species, which includes a selected apolipoprotein by means of capturing antibodies specific to the apolipoprotein, the capturing antibodies being attached to a solid phase; detecting and measuring at least one fraction of lipid in the intact lipoprotein species; and detecting and measuring at least one expressed epitope on at least one apolipoprotein in the intact lipoprotein species by means of labeled probing antibodies specifically binding thereto. In a preferred embodiment, capturing antibodies are monoclonal, mixtures of monoclonals, or polyclonals; in another preferred embodiments, probing antibodies are monoclonals, mixture of monoclonals or polyclonals. In embodiments comprising lipoprotein determinations, the concentration of lipids is determined by means of a detectable agent which selectively is incorporated in lipids, that is, stains or dissolves in, lipids. In a particularly preferred embodiment, the detectable agent which selectively is incorporated in lipids is a fluorescent dye. In another preferred embodiment using a limited number of capturing antibodies, a variant method is developed to detect and measure at least one lipid fraction and at least one expressed apolipoprotein epitope on a constant number of intact lipoprotein particles. In another embodiment of the method, the determination of lipids and the determination of apolipoprotein expressed epitopes can be carried out as a panel, individually, or in any combination. In yet another embodiment of the method, the sample comprises a class of lipoproteins isolated from a specimen.

The methods of the invention comprising the determinations on intact lipoproteins may be used to identify subjects at risk for coronary artery disease. In alternative embodiments, the methods described may be applied to samples of selected lipoproteins isolated from a specimen, to intact lipoproteins in plasma, or may be applied to the determination of the composition of intact lipoproteins in cells, or parts of cells.

According to yet another aspect of the invention, there is provided a method of studying dynamic patterns of lipoprotein composition in a subject during a fasting-feeding cycle, comprising obtaining a fasting blood sample from the subject; continuing to obtain blood samples from the subject at intervals over a period of time after allowing subject to ingest food; determining the lipoprotein composition in each the sample according to the method of the invention; and observing changes in lipoprotein composition occurring among the samples. According to this aspect of the invention, the methods may be used to classify epitopes of apolipoproteins on intact lipoproteins as either variable or stable; to determine the impact of variable epitope expression on clinical conditions associated with abnormal lipid metabolism; and to identify and evaluate abnormal metabolic processes associated with the absorption of ingested lipids, the efficiency of lipolysis, Lipoprotein lipase (LPL) complex activity, or the function of variable or stable epitopes.

According to yet another aspect of the invention, there is provided a kit for carrying out determinations of intact lipoproteins, comprising at least one multiwell microtiter plate, the surface of the wells being coated with capturing antibody specific for a selected apolipoprotein species; at least one probing antibody, the antibody having a specificity for an expressed epitope of an apolipoprotein present in the intact lipoprotein, the probing antibody being labelled; and a detectable agent, capable of selectively being incorporated in lipids. In a preferred embodiment, the probing antibody is a polyclonal or monoclonal antibody or a mixture of monoclonal antibodies having a specificity for at least one selected expressed epitope on an apolipoprotein. In other preferred embodiments, at least one plate in the kit is coated with antibody having a different apolipoprotein specificity from that of the others. In a particularly preferred embodiment, the kit comprises an ELISA procedure wherein the probing antibody is labelled with an enzyme, and the kit further comprises a substrate for the enzyme.

DETAILED DESCRIPTION OF THE INVENTION

The present invention is a clinical test procedure, lipid moiety dynamics/expressed epitope immunoreactivity dynamics, LMD/EEID, which allows the simultaneous determination of the species and concentrations of lipid components and the apolipoprotein components of intact native lipoproteins. The flexibility and scope of the test concept allows its application to a number of diverse clinical or research lipid studies.

According to the concept, intact native lipoprotein particles from a specimen such as, for example, human plasma, are isolated and separated into distinct species, without disruption of the lipid-protein complex by centrifugation or solvent extraction, and each species immobilized. The lipoprotein species is conveniently isolated on a solid phase by means of an agent that specifically binds one species of apolipoprotein, specifically a capturing antibody coating the solid phase, and capable of binding to a certain apolipoprotein in the lipoprotein particle. Determinations of lipids and apolipoproteins, either or both, are then carried out on the individual intact native particles. Determinations of the lipid or apolipoprotein components of the lipoprotein may be qualitative, semi-quantitative or quantitative. Accordingly, the lipids present in the lipoprotein may be analyzed for total lipids and neutral lipids. They may also be analyzed for a distinct, clinically relevant lipid fraction, such as, for example, cholesterol or triglycerides. The methods used for these determination are not restricted as to type and may be selected on the basis of convenience or accuracy, as for example, colorimetric, fluorescent, radiometric, enzymatic, or measurement of some physical property. In preferred embodiments, the methodology is capable of being adapted to an automated procedure, as for example, enzyme based colorimetric assay of an ELISA test, that can be read using an automated plate reader. In a particularly preferred embodiment, lipid classes of the lipoprotein, neutral and total lipids, are measured and distinguished by incorporating in them a lipid selective fluorescent dye, Nile Red. Apolipoproteins of the isolated intact native lipoprotein particle are determined on the basis of their expressed epitopes, that is immunologically distinct regions of the protein which are exposed and free to bind natural ligands, such as enzymes, antibodies and cell receptors, and therefore, by inference, not coated with lipid. Determination of the expressed epitopes of the apolipoproteins may be made using any ligand thereto to which a detectable label has been attached. Preferably, the ligand is an antibody and in a preferred embodiment of the invention, the ligand is a monoclonal antibody. The specificity of the antibody used to detect expressed epitopes is determined by the purpose of the assay. For example, if the comparative lipid load on a given lipoprotein species is to be determined, an antibody of broad specificity, covering all normally expressed epitopes, such as a polyclonal antibody or mixture of monoclonals, will be used; if the availability of a specific, functionally important epitope is to be determined, a highly specific monoclonal antibody will be used.

As in the case of the detection of the lipid moieties described above, detection of the expressed apolipoproteins epitopes, by means of a label attached to a specifically binding antibody, may be made by any convenient available methodology. Accordingly, the label of the antibodies may be enzymes, which react with a substrate to give a colorimetric or fluorometric signal, or the antibodies may be radiolabelled. Alternatively, the antibodies may be labelled after they have bound the apolipoprotein epitopes by a second antibody having a specificity for them and which itself carries a label. For example, mouse monoclonal antibodies bound to apolipoproteins may be detected by enzyme labelled rabbit anti-mouse IgG antibodies. The detection of bound antibodies may be amplified by the use of avidin-biotin linkages of antibodies and labels, as is well known in the art.

Carrying out tests on intact lipoproteins provides two types of information not available with conventional lipid and apolipoprotein determinations. First by providing data on lipid moiety and apolipoprotein types within each lipoprotein class in the several metabolic stages, the remodeling of lipoprote in species can be followed, and abnormalities in intestinal absorption or metabolic clearance identified. Secondly, by determining apolipoprotein not as total concentration, but in terms of their expressed, epitopes, the clinical test follows the functional apolipoprotein concentration, which should correlate with the ability of these apolipoprotein epitopes to regulate the lipoprote in transport process by interacting with enzymes and receptors. Further, the tests permit one to correlate the process of lipolysis with changes in the functional activity of the apolipoproteins.

LIPID MOIETY DYNAMICS (LMD)/EXPRESSED EPITOPE IMMUNOREACTIVITY DYNAMICS (EEID) OF APO $B_{100}$- OR APO $A_1$-CONTAINING LIPOPROTEINS

LMD/EEID is carried out based on the isolation of intact lipoproteins on the basis of their characteristic apolipoproteins, and is described in the embodiment of an ELISA assay Examples 1–3.

This test format comprises the isolation of intact lipoprotein species having a common apolipoprotein. This species is conveniently isolated on a solid phase by means of an agent that specifically binds one species of apolipoprotein. The agent is bound to the solid phase either by adsorption thereon or by covalent attachment to a capturing species. This capturing species is preferably an antibody, but it may also be another agent having specificity for apolipoprotein.

The test is most conveniently carried out in multiwell microtiter plates, such as Nunc Immunowells, (Irvine Scientific, Santa Ana, Calif.) but may also be performed in other solid phase media. The isolation of classes of intact lipoproteins should not be limited to techniques using only antibodies as binding agents. In the future, it is to be expected that other probes will be developed which specifically will bind to certain apolipoproteins in a nonimmune fashion (similar to protein A or lectins).

In the preferred test structure of the microwells, adjacent groups Of wells or sets of plates may be coated with antibodies to different apolipoproteins, such as for example apo AI and AII, associated substantially with HDL and chylomycrons and apo $B_{100}$ associated substantially with VLDL and LDL. In this way, an entire lipoprotein analytical profile can be generated.

Intact lipoproteins are then separated from a sample of a specimen, such as for example, bodily fluids, tissue or cells, by placing a volume of the sample in each well and allowing the lipoproteins to be bound thereto. The specimen may be any biological material containing lipoproteins, such as plasma or lymphatic fluid, or it may be the fluid portion of cells, such as those of the liver. The sample may be the crude specimen, or it may be a separated fraction, for example, a lipoprotein enriched sample, or a sample of an isolated lipoprotein class. The optimum time necessary for lipoprotein to bind quantitatively to the support can be determined empirically, by sequential trials.

After the intact lipoproteins are bound to the support through the apolipoprotein group, unbound lipoproteins are removed by rinsing with a buffer solution. Sites of the support which are available to non-specific binding are blocked by treatment with a solution containing a protein such as for example albumin or gelatin.

Analysis of the bound intact lipoproteins in each well then proceeds with the determination of the lipid moiety (LM) and/or expressed epitope immunoreactivity (EEI).

Lipid moiety will be determined on microtitre well using gelatin as blocking agent or any other suitable nondelipidating agent. Albumin should be eliminated as a blocking agent due to its ability to bind Nile Red and, therefore, to interfere with lipid moiety staining with Nile Red. Studies should be carried out to see if it is possible to determine LM in the same well prior or thereafter EEI determination. Lipid moiety is determined by means of a detectable agent which is incorporated in lipids. In a preferred embodiment, the detectable agent is a fluorescent dye, and in a particularly preferred embodiment, it is Nile Red (also termed Nile Blue Oxazone, Molecular Probes, Inc., Junction City, Oreg.). Nile Red is incorporated in both neutral and polar lipids (phospholipids), but can determine each class independently by adjustments in concentration and the excitation and emission wavelengths (Greenspan and Fowler, Kodak Laboratory Chemicals Bulletin, 56(3):1–4(1985). A yellow-gold fluorescence at excitation of 450–500 nm and emission >528 nm results from binding to cholesterol, cholesterol ester and triglycerides (neutral lipids), and a red fluorescence at excitation of 515–580 nm and emission >590 nm results from total lipid binding (neutral lipids and phospholipids). Fluorescence may be read with automated microtiter plate scanning devices having fluorescent capability, as for example, Fluoroscan II, (marketed by Flow Laboratories, McLean, Va. 22102). The use of organic solvents to dissolve lipid staining dyes is to be avoided, since these will also dissolve lipoprotein lipids. The agent MOLECUSOL™, cyclodextrines, Pharmatec, Inc., Alachua, Fla. 32615), is a useful solvent which avoids this difficulty.

Expressed apolipoprotein epitopes are determined by the binding of specific labeled probing antibodies. In most cases, the expressed epitopes to be detected will be those of that apolipoprotein which has been captured on a solid surface, but it can also be the expressed epitopes of other apolipoproteins associated with the same lipoprotein, such as, for example, apolipoprotein E particles on VLDL particles which have been captured by means of the associated Apolipoproteins B particles. Again, these antibodies may be monoclonal, mixture of monoclonals or polyclonals and may be produced as described below. The preferred probing antibody reagent in studying apolipoprotein dynamics should have a precisely known epitope specificity directed ideally against all known expressed epitopes of a given apolipoprotein on a native lipoprotein in fast.

The label attached to the probing antibodies may be an enzyme, such as peroxidase, alkaline phosphatase, or beta-galactosidase, as are commonly used in ELISA assays. These enzymes react with appropriate substrates to produce a colored compound, the concentration of which can be measured by its absorbance. In a preferred embodiment of the test, however, the interaction of alkaline phosphatase or beta-galactosidase with a substrate methyl-umbelliferonyl phosphate generates a fluorescent product, detected by the same automated system used to measure the Nile Red binding.

Chemiluminescent enzyme-linked immunosorbent assay can be used also in apolipoprotein quantification. When the tagging enzyme is peroxidase, the detection system is Luminol/$H_2O_2$ (Stevens, P. et al., Lab Res. Methods Biol. Med. 4:205 (1980). The amount of light produced in these reactions is quantified using appropriate light measuring devices such as ML 1000 microplate luminometer (Dynatech Lab, Inc., 14340 Sully Field Circle, Chantilly, Va. 22021). Preferably, when either fluorescent or chemiluminescent signals are to be read, the test is carried out on black plates.

THE VARIANT TEST OF LMD/EEID USING A CONSTANT NUMBER OF LIPOPROTEIN PARTICLES

The initial test does not discriminate between increase of number of lipoprotein particles vs. the increase in size of the same number of particles as a result of loading with lipids subsequent to meals.

The variant of the initial test LMD/EEID is a test studying the dynamics of lipid moiety and expressed epitope immunoreactivity on a constant number of lipoprotein particles in each well in fast-feeding cycle (Examples 4–6).

In order to ensure that a constant number of lipoprotein particles are captured, the capturing antibody should be a limiting factor (i.e., in a very limited number). The number of capturing antibodies coating each well should be chosen in such a way as to always be able to capture from undiluted samples with a variable number of lipoprotein particles (fast, 3, 6, 9, 12, and 24 hours after a meal) the same number of particles. Therefore, this variant of the test studies a constant number of lipoprotein particles in each well, and it is designed not to be quantitative.

In spite of the same number of particles being captured in each well, the type of the particles are not the same as a result of the meal (in fasting state, predominance of LDL; in postprandial samples, predominance of VLDL and chylomicrons).

In spite of capturing the same number of lipoprotein particles in each well, the readings of lipid moiety (LM) and expressed epitopes immunoreactivity (EEI) are not expected to be the same (as one may assume) in fasting samples of different individuals or in samples obtained at different times after a fatty meal. This is due to mutual interaction of lipids and apolipoprotein epitopes characteristic for lipoprotein particles.

The variation in readings in fast is due to different degrees of masking of apolipoprotein epitopes by lipids in different individuals.

The variation in readings in samples obtained at different times after a fatty meal in the same individual is due to masking-unmasking of apolipoprotein epitopes by lipids subsequent to a fatty meal.

Obviously the readings for LM and EEI in this variant test will be lower than the readings in the standard test.

The same number of particles are exposed to probing antibodies, monoclonals, mixture of monoclonals, or polyclonals with precisely known specificity, tagged with enzyme or other label (EEID). In the same manner the same number of captured particles are exposed to the staining with Nile Red (LMD).

Any differences detected between fast and postprandial samples will give information about masking, nonexpression, (decreased EEID) and unmasking, expression (increased EEID) of apolipoprotein epitopes (B100 or $A_f$, etc.). At the same time, the Nile Red staining the same number of captured particles (in fast and postprandial LMD) will offer an indication regarding the size of the particles when compared with fasting state (increased lipid moiety indicating large sized particles, the same lipid moiety indicating small sized particles).

The results are expressed in optical densities, fluorescent units or light units per well using appropriate devices (photometer, fluorometer, or luminometer). Certainly this represents only relative concentration for lipids and apolipoprotein moiety due to the fact that only a limited number of lipoprotein particles are studied.

The standard for apolipoprotein and lipid moiety will be a secondary standard from IUIS, which is a lyophilized pool of sera or a fresh pool of normal plasma. This will be compared with a fasting sample. The samples obtained at 3, 6, 9, 12, and 24 hours after meals will be compared with the fasting sample. Alternatively, all these samples could be compared with corresponding samples obtained at the same intervals from healthy normal subjects.

Fresh samples are preferred, due to changes in apolipoprotein and lipid moieties which occur with storage. The tremendous advantages of this variant are:

1. Small quantities of capturing antibodies with subsequent savings.
2. Obviates the need of diluting the samples with all the consequences regarding precision.
3. The initial test does not discriminate between an increase in the number of lipoprotein particles vs. an increase in the size of the same number of particles as a result of loading with lipids subsequent to meals.

Having the number of captured particles constant, the variant test can better evaluate if the response to a meal is with larger sized particles, as suggested by an increase of lipid moiety after feeding. EEID is studied in the same samples offering the information of epitope masking by lipids and unmasking of epitopes secondary to lipolysis. An epitope masking event will be suggested by an increase in lipid moiety (LM) and decrease in EEI in the same sample. An epitope unmasking event will be suggested by a decrease in LM and an increase in EEI in the same sample.

EPITOPE SCANNING OF PROTEIN MOLECULES OTHER THAN LIPOPROTEINS

Epitope scanning or molecular scanning using as probing agents tagged monoclonal antibodies can be performed on any protein molecules such as: surface proteins of viruses, bacteria, or cell membranes, proteins involving coagulation, hormones, complement proteins, enzymatic protein Lecithin-cholesterol acyltransferase and Lipoprotein lipase (LCAT and LPL), etc.

First the molecule in the study has to be isolated in pure form. Then, monoclonal antibodies are developed for each epitope on the molecule in the usual fashion. The specificity of each monoclonal is precisely characterized. Another alternative of obtaining monoclonal antibodies is using as immunogen isolated or synthesized peptides from the known sequence of said molecules.

Each isolated monoclonal or their mixture raised to epitopes expressed in normal molecules, would represent a powerful reagent to use for the "epitope scanning" for the presence of all (when a mixture of monoclonals is used), or certain (when one monoclonal is used) epitopes on the intact molecule.

From sequence studies or peptide fragment studies, each epitope or group of epitopes will be assigned a certain function on said molecule (such as ligand to interact with receptors or other molecules, enzyme activator or inhibitor, etc.). Example 7 suggests performing epitope scanning in microtiter plates.

In order to compare protein molecules from standard and sample, the number of captured molecules should be the same. This is accomplished using a very limited number of capturing antibodies, coating each well, to create such an excess of antigen that it would always saturate the limited number of capturing antibodies. This is accomplished not only by decreasing the amount of capturing antibodies in each well, but also using nondiluted specimens and increasing the time and temperature for the capturing step. The non-captured molecules will be washed away. As a result, the same number of molecules captured from standard or sample will be "scanned" thereafter with probing antibodies which are monoclonals, mixture of monoclonals, or polyclonals with precisely known specificity tagged with enzyme or other label.

Any differences detected when these scanned molecules are compared with standard would suggest either lack of epitope expression or abnormal epitope expression. If a monoclonal antibody with known specificity is subsequently used, the defect is narrowed to one single epitope.

Certainly to detect such small differences in epitopes, the detection system should use very sensitive labels (fluorescent, chemiluminescent, bioluminescent, radioisotope, etc.) and appropriate detecting devices (fluorometer, luminometers, etc.).

The result would be expressed in fluorescent units or light units per well.

The absence of an epitope or group of epitopes as inferred by lack of binding of probing antibody on studied molecule will indicate abnormality.

Using this technique, the epitope absence or malformation can be rapidly detected and linked to loss of a specific function of the molecule. It should be clearly understood that epitope scanning is not a quantification of the analyte. It is just an immobilization of a certain number of molecules in order to be subsequently scanned.

Preparation of Appropriate Antisera:

1. The Immunogen It was previously shown that native hololipoprote in particles should be used as immunogens (Schonfeld, G. et al. *Jour. Clin. Invest.* 64: 1288–1294 (1979)). It is assumed that conformational epitopes are functionally important, and may have crucial metabolic significance (Schonfeld). It is also known that aged or degraded apolipoproteins have a distinct antigenic response from native molecules (Curtiss, L. and Edgington, R. *J. Biol. Chem.* 260:2982–2993(1985)). Therefore the immunogen should be prepared from freshly collected plasma, using EDTA, antimicrobials, and antiproteolytic agents in order to minimize the chance of producing artifactual epitopes which are immunogenic. The plasma should be collected and pooled from several normal subjects, in fast. The immunogens in these plasma samples will thus comprise lipoprotein particles having native, expressed epitopes in fast. Using as immunogen, native lipoprotein particles at the peak of absorption after a meal may generate antibodies to new conformational epitopes occurring on apolipoprotein molecules as a result of a meal.

2. The capturing Antibody may be monoclonal, mixture of monoclonals, or polyclonal. They should be developed to epitopes of the apolipoprotein which are not lipid dependent, and hence always available or unmasked, even in lipoproteins that are heavily loaded with lipid. Polyclonal antibodies having the required specificity may be raised by immunizing animals with native lipoprotein which is heavily coated with lipid, so that only the apolipoprotein sites which are not lipid dependent are available as immunogens. Monoclonal antibodies to lipid independent sites may be raised according to the procedures described below.

3. Probing Antibody conjugated to enzyme, or other markers should be specific to a precisely known epitope or epitopes. For this reason, probing antibodies are preferably monoclonals, but can also be a mixture of monoclonals or polyclonals. Monoclonal antibody to specific lipid dependent or non-lipid dependent sites of selected apolipoproteins may be raised, according to the procedure of Kohler and Milstein, *Nature* 256 (8): 295–297 (1975). The production of such antisera can be facilitated by means of commercial kits (HyBRL Screen™ kit, Cat. No. 9505SA, Bethesda Research Labs, Gaithersburg, Md. 20877) for production and screening. The amino acid sequence of the major apolipoproteins are known (Mahley, R. et al., *Jour. Lipid Res.* 25:1277–1294 (1984) and using these sequences, immunogenic peptides representing all epitopes can be manufactured commercially (Cambridge Research Biochemicals, Valley Stream, New York, N.Y. 11580) to facilitate monoclonal antibody production.

Antisera of various levels of specificity are useful in several applications of the LMD/EEID test system described below. For example, it would be desirable to use a polyclonal antisera of a broad specificity or a mixture of several monoclonal antisera to quantitate total expressed epitopes of a given apolipoproteins, however, in determining the expression of a specific functional epitope, a monoclonal of high specificity would be required. The determination of apolipoprotein composition in intact lipoprotein species requires the use of a corresponding standard. A secondary reference serum standard is available from the Center for Disease Control (CDC) for use in lipoprotein testing for risk of atherosclerosis and associated cardiovascular disease, and commercial manufacturers of diagnostic equipment have prepared secondary standards based on the CDC secondary reference serum standard (for example, Beckman Instruments, Fullerton, Calif.).

Primary standards of purified apolipoproteins have proved to be unreliable and are structurally not appropriate standards for determining expressed epitope concentrations. It is preferable and advisable, considering the more functional nature of the LMD/EEID procedure, to use the secondary standard reference sera, and to express results of apolipoprotein epitopes and lipid moieties in relative rather than absolute units. The relative units in which results are expressed could be the raw optical density units or relative fluorescence units. The standard curve is prepared for ech plate and should have a good working range and a good sensitivity. The method is evaluated for precisions, specificity, sensitivity and accuracy.

Mechanisms and Interpretations of the LMD/EEID Test

The performance of the tests, its anticipated patterns and their interpretation, are best understood in the light of present knowledge of lipoprotein metabolism and apolipoprotein structure.

Some areas of the molecule represent variable epitopes, an expression of genetic polymorphism present only on some apolipoproteins; other areas represent stable epitopes present on all apolipoprotein molecules and specific for each apolipoprotein. Both types of epitopes are the object of our quantitation. Some of these stable epitopes are always masked or always unmasked whether in a fasting or post prandial subject; others are temporarily masked either by lipids or by folding/unfolding and become unmasked in a certain moment of apolipoprotein physiology. Both of these types of stable epitopes may be functionally active in the recognition of receptors, or the activation or inhibition of enzymes. The variable epitopes which are responsible for the genetic apolipoprotein polymorphism can be studied with the same LMD/EEID test using appropriate antibodies developed to these variable regions on the molecule.

FIG. 1 demonstrates the hypothetical dynamics of lipid moiety and expressed epitope/epitopes immunoreactivity on Apo $B_{100}$- and Apo $A_1$-containing lipoprotein particles after a unique fatty meal in normals:

(1) represents lipid moiety dynamics (LMD).

(2–4) represents different patterns of expressed epitope immunoreactivity dynamics (EEID).

Any pattern of dynamic response is anticipated and should not be limited to those suggested in the drawings.

On curve 1:

The AB segment of the curve corresponds to the endogenous pathway stimulated by intestinal absorption, where B represents the peak of absorption. The BC segment of the curve corresponds to lipolysis and cellular uptake; and the CD segment of the curve corresponds to nocturnal lipolysis from fatty tissue and nocturnal traffic of lipids.

Panel 1 indicates apo $B_{100}$-containing lipoprotein dynamics (lipid moiety and expressed epitope immunoreactivity of apo $B_{100}$). This part of the diagram explores VLDL, IDL, and LDL particles.

Panel 2 indicates apo $A_1$-containing lipoprotein dynamics (lipid moiety and expressed epitopes immunoreactivity of apo $A_1$). This part of the diagram explores chylomicrons and HDL particles. In this panel only two hypothetical curves are drawn.

In panel 1, curves 1 and 2 have an opposite direction, suggesting that the lipid moiety increase is associated with masking of apo $B_{100}$ epitopes and the lipid moiety decrease due to lipolysis is associated with unmasking (increase of apo $B_{100}$ expressed epitope immunoreactivity) as a function of time. Another anticipated pattern is pictured by curves 1 and 3 wherein both have the same direction, suggesting that the lipid moiety increase parallels the expressed epitope immunoreactivity of apo $B_{100}$ increase indicating that no masking of apo $B_{100}$ epitopes occurs. This assumes that the number of lipoprotein particles increases after a meal.

The last suggested pattern is that of curves 1 and 4, which picture an increase and decrease of lipid moiety associated with a constant expressed epitope immunoreactivity of apo $B_{100}$. The assumption can be made that a constant number of lipoprotein particles are loaded and unloaded with lipids after a standard fatty meal.

All classes of lipoprotein particles comprise a continuous spectrum from small size interdigestive or fasting-state particles to large size postprandial particles. In small size particles, more epitopes are expressed on the apolipoprotein moiety than on larger sized particles, where they become masked by lipids. A fasting sample, then, serves as an individual "control" for lipid moiety and expressed epitope immunoreactivity of apo $B_{100}$ and apo $A_1$-containing lipoprotein particles.

The AB segment of the curve from FIG. 1 is developed using the samples at three and six hours after a fatty meal. If the small sized particle (the particles characteristic of the interdigestive state) increases in number as a response to a unique fatty meal, the same epitopes are expressed on all particles and the same lipoprotein moiety is on every particle. The expressed epitope immunoreactivity increases parallel with lipid moiety (FIG. 1, curve 1 and 3). If the large sized particles increase in number (postprandial type lipoprotein particles) as a response to a unique fatty meal, the lipid moiety will increase and the expressed epitope immunoreactivity will decrease because a masking effect of epitopes will occur (FIG. 1, curves 1 and 2). This segment of the curve will therefore explore intestinal absorption and liver production of lipoprotein particles.

The BC segment of the curve is developed using the samples at nine and twelve hours after the fatty meal. If the response to the fatty meal was with small sized particles, characteristic for the interdigestive state, the decrease of lipid moiety will parallel the decrease in expressed epitope immunoreactivity (FIG. 1, curves 1 and 3). If the response to a unique fatty meal is with large sized particles, characteristic to the postprandial state, the lipid moiety will decrease and the expressed epitope immunoreactivity will increase due to unmasking of epitopes subsequent to intravascular lipolysis (FIG. 1, curves 1 and 2). The lipolysis transforms large sized particles to small sized particles with subsequent expression of new epitopes. This segment of the curve will therefore explore the lipoprotein clearance caused by intravascular lipolysis and cellular uptake of lipoproteins.

The CD segment of the curve is developed using the 24 hour samples ( FIG. 1, curves 1 through 4). It explores nocturnal lipolysis from fatty tissue and liver production of lipoproteins particles in the interdigestive state. Certainly a response to a unique fatty meal with both small and large particles is possible.

Figure 2:
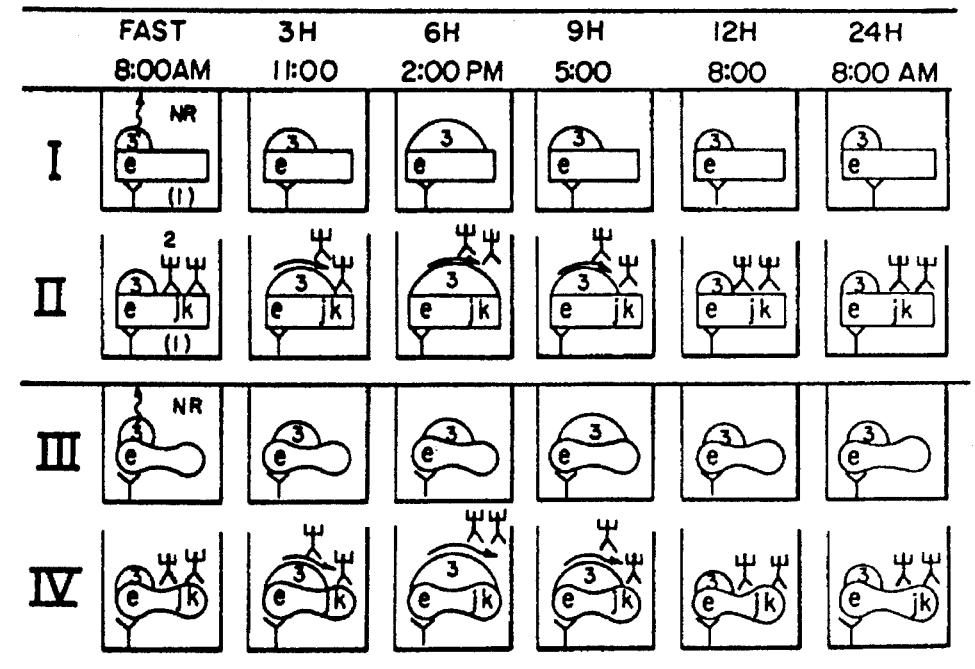
FIG. 2 is a general diagram depicting the dynamics of the Lipid Moiety Dynamics/Expressed Epitope Immunoreactivity Dynamics (LMD/EEID) test in the fasting-feeding cycle (horizontal rows) and a profile of the simultaneous tests (vertical rows).

FIG. 2 represents the general diagram of test structure over a 24 hour period.

(1) represents capturing antibody.
(2) represents probing antibody.
(3) represents lipid moiety.
(e, j, k) represents epitopes on apolipoprotein molecule.
↑ signifies the fluorescence Of Nile Red.
→ indicates inability of antibodies to react with specific epitopes.
(e) epitope binding to capturing antibody.
(j–k) epitope binding to probing antibody.
Panel I: LMD of Apo $B_{100}$-containing lipoproteins.
Panel II: EEID of Apo $B_{100}$ in Apo $B_{100}$-containing lipoprotein particles (multiple or single epitopes).
Panel III: LMD of Apo $A_1$-containing lipoproteins.
Panel IV: EEID of Apo $A_1$ in Apo $A_1$-containing lipoprotein particles (multiple or single epitope).

Figure 3:
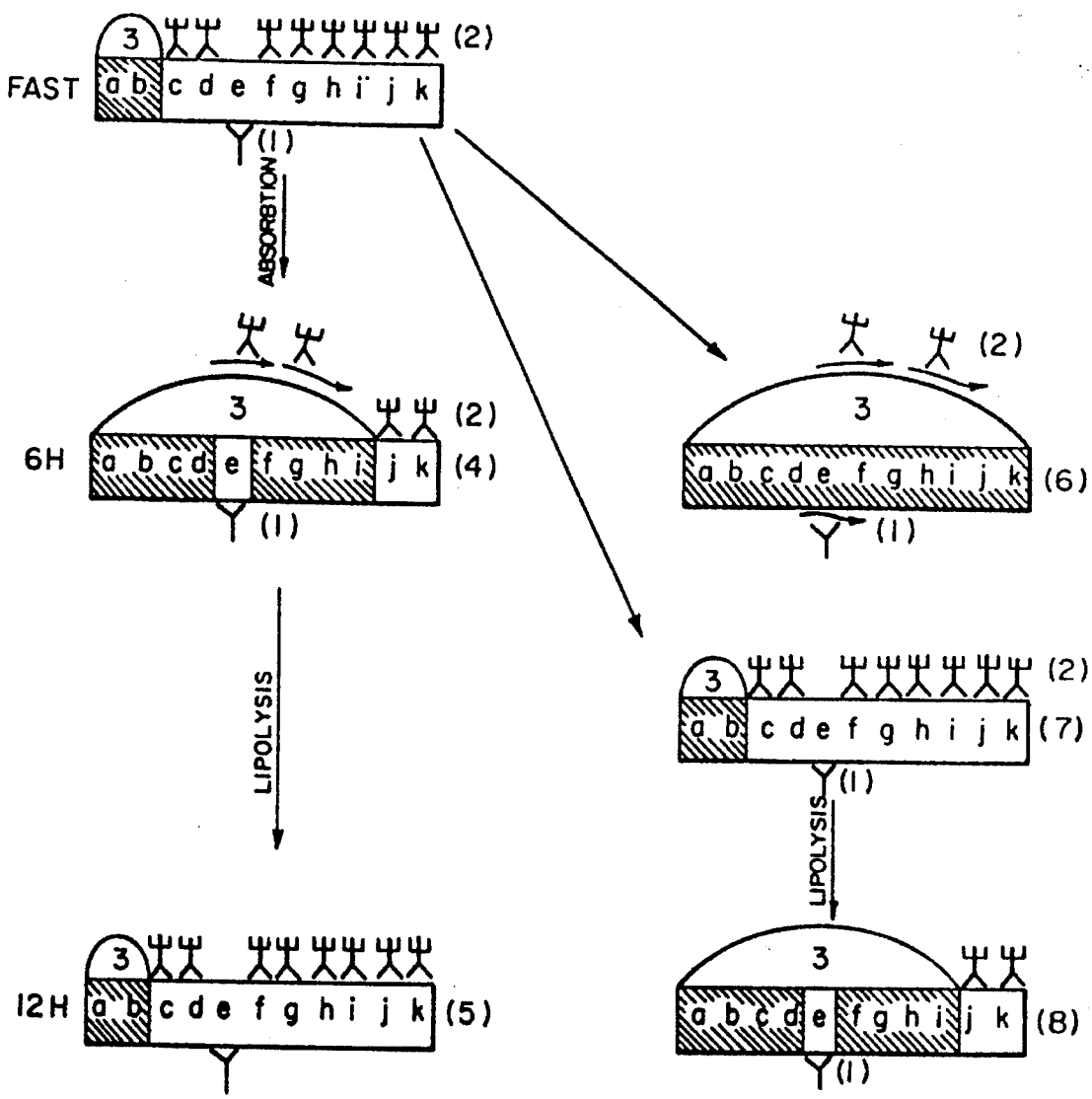
FIG. 3 is a schematic diagram which describes the expressed epitopes immunoreactivity dynamics of apo $B_{100}$, apo $A_1$, or any other apolipoprotein having all or most of the epitopes subject to study.

FIG. 3 demonstrates the expressed EPITOPES immunoreactivity dynamics (of apo $B_{100}$ or apo $A_1$ or any other apolipoprotein).

(a–k) epitopes on apolipoprotein molecule.
(a–b) native masked epitopes.
(1) Monoclonal capturing antibody with specificity for "e" epitope.
(2) polyclonals or mixture of monoclonals with precisely known specificity conjugated with enzyme, each binding to a specific epitope (probing antibody).
(3) Lipid moiety in fast masking epitopes a and b.
→ inability of antibodies to react with specific epitopes. Shaded area indicates lipid masked epitopes.

The left side of the figure presents hypothetical normal dynamics in fast, 6 hours (diagram 4), and 12 hours (diagram 5) after a meal.

The right side of the figure presents hypothetical abnormal dynamics 6 hours (diagrams 6 and 7) and 12 hours (diagram 8) after a meal.

(4) lipoprotein corpuscle at 6 hours after fatty meal. It is assumed that lipid moiety (3) increases and masks additional epitopes c, d, f, g, h, and i. Epitope "e" is nonlipid dependent and is still available to react with capturing antibody (1). The only available epitopes for probing antibody (2) are j and k. They are scanned by polyclonals or mixture of monoclonals (2). In this situation, lipid moiety increases and apolipoprotein immunoreactivity decreases. This explores intestinal absorption and hepatic production of lipoprotein particles as a response to a standard fatty meal.

(5) Lipoprotein corpuscle at twelve hours after standard fatty meal, as a result of LPL activity, lipolysis occurs, lipid moiety (3) decreases and c, d, f, g, h and i epitopes are unmasked. As a result of this, more epitopes are exposed to probing (scanning) antibody, and immunoreactivity of apolipoprotein moiety increases. (6), (7), and (8) suggest abnormal conditions:

(6) Depicts the situation six hours after a standard meal when all epitopes a–k are masked by the lipid moiety. As a result, epitope "e" for capturing antibody (1) or for probing antibodies j and k are not available to react with their corresponding antibodies. The lipoprotein particle is not captured (arrow separating antibodies from apopoprotein). This well will have the same composition as a blank (all the reagents minus antigen). Therefore, I call this situation the "blank effect."

(7) Lipoprotein particle six hours after standard meal looks the same as the particle in fast. Only a and b epitopes are masked and the lipid moiety (3) is small. This indicates poor intestinal absorption of lipids.

(8) Lipoprotein particle at twelve hours after standard meal looks the same as the particle in the peak of absorption at six hours (c–d and f–i epitopes masked by lipid moiety). This may indicate defective lipolysis.

Figure 4:
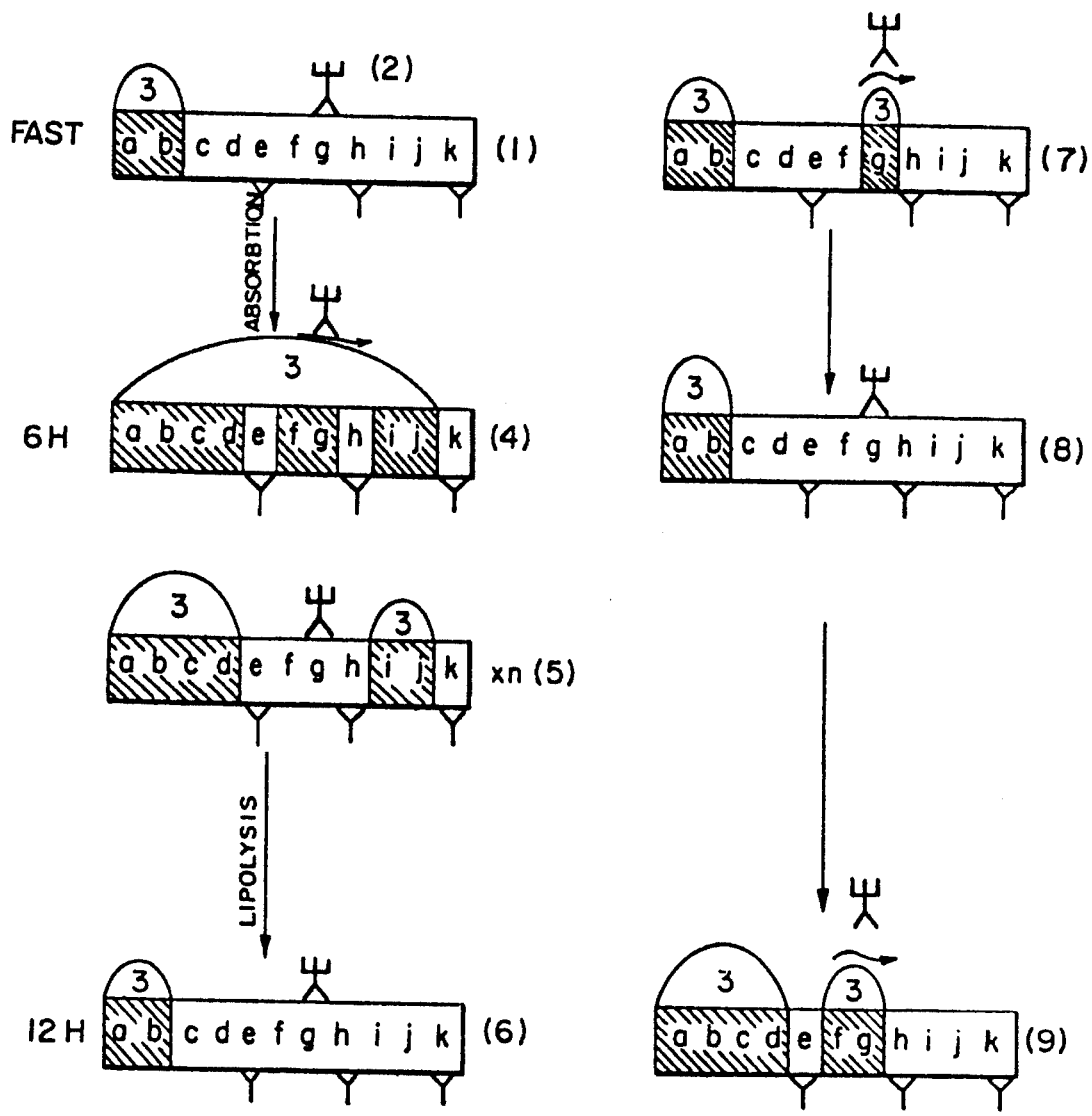
FIG. 4 is a schematic diagram which describes the expressed epitope immunoreactivity dynamics of an apolipoprotein having a single epitope subject to study.

FIG. 4 represents single epitope expressed immunoreactivity dynamics of a given apolipoprotein.

(a–k) epitopes on an apolipoprotein molecule
(g) The epitope reacting with probing monoclonal antibody. This is the epitope whose dynamics is studied. This epitope may be functionally significant (activator or inhibitor of an enzyme, or receptor recognition site).
(a–b) native masked epitopes.
Shaded areas indicate lipid masked epitopes.
→ indicates inability of antibody to react with specific epitopes.

The left side of the figure represents hypothetical normal dynamics in fast, six hours (Diagram 4 and 5), and 12 hours (Diagram 6), after a meal.

The right side of the figure represents hypothetical abnormal dynamics in fast (Diagram 7), six hours (Diagram 8), and 12 hours (Diagram 9) after a meal.

(1) polyclonal capturing antibody with specificity for e, h, and k epitopes.
(2) probing monoclonal conjugated with enzyme binding to epitope g, whose dynamic is studied.
(3) Lipid moiety in fasting state masking a and b epitopes.
(4) lipoprotein corpuscle six hours after a fatty meal. The lipid moiety is assumed to increase and mask epitopes a–d, f–g, i–j. The studied epitope g is masked; therefore, probing antibody cannot bind (arrow separating the epitope from antibody). No enzymatic reaction will take place in this well. The capture of the particle is possible and will take place because epitopes e, h, and k are available for capturing antibody. The capturing of the lipoprotein particle will be detected by the Nile Red staining the lipid moiety in an alternate plate.

(5) depicts another possible response of a lipoprotein particle six hours after the standard meal with epitopes f and g unmasked. Only epitopes a–d and i–j are masked by the lipid moiety. The e, h, and k epitopes are available for capturing antibodies. The symbol X(n) signifies a possible increase in the number of lipoprotein particles as a response to a fatty meal. Therefore, the number of "g" epitopes will increase.

(6) Lipoprotein particle 12 hours after the standard fatty meal. As a result of LPL activity, lipolysis occurs. The lipid moiety shrinks unmasking c–d, f–g, i–j epitopes.

(7) through (10) suggest abnormal conditions:

(7) epitope g is masked in fast, unlike in normal conditions. Therefore, epitope g is not available to react with probing "scanning" antibody (arrow separates the epitope from the antibody).

(8) epitope g is unmasked at six hours after a meal when in a "normal epitope dynamics," the g epitope is masked. The lipid moiety is small suggesting malabsorption.

(9) the lipoprotein particle at twelve hours after the fatty meal has still masked f and g epitopes in contrast with what is happening in anormal dynamics (6), when the epitope g is unmasked. The monoclonals will not bind epitope g as suggested by the separating arrow. This may indicate poor lipolysis. The lipid moiety detected in an alternative well using Nile Red will be large for what is usually detected at 12 hours in a normal subject (Diagram 6).

Figure 5:
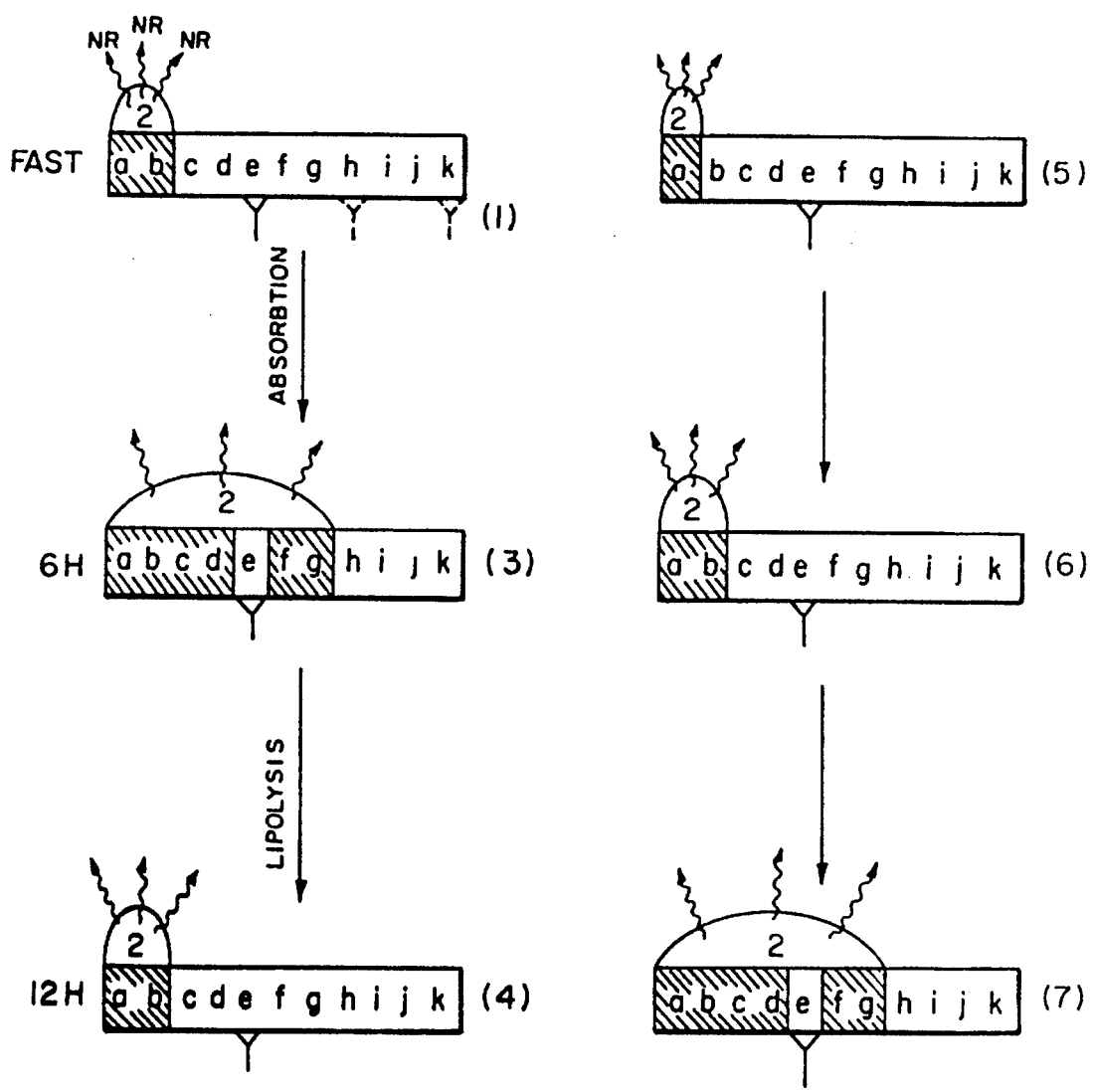
FIG. 5 is a schematic diagram which describes lipid moiety dynamics in normal and various abnormal conditions.

FIG. 5 demonstrates lipid moiety dynamics.

This dynamics can be explored on an apo $B_{100}$-containing particles (VLDL, IDL, or LDL) or apo $A_1$-containing particles (chylomicrons and HDL). Any captured lipoprotein particles can be exposed to the same study.

(a–k) apolipoprotein epitopes. Shaded areas indicate lipid masked epitopes.

↑ signifies the fluorescence of Nile Red.

The left side of the figure indicates hypothetical normal dynamics in fast, six hours (Diagram 3), and twelve hours (Diagram 4) after a meal.

The right side of the figure indicates hypothetical abnormal dynamics in fast (Diagram 5) six hours (Diagram 6) and twelve hours (Diagram 7) after a meal.

(1) capturing antibody can be monoclonal, mixture of monoclonals, or polyclonal. No probing antibody is necessary. After staining the lipid moiety with Nile Red, the plate will be read with an appropriate device (for example Fluoroscan II from Flow Laboratories).

(2) lipid moiety stained with Nile Red (NR) masking in fast only epitopes a and b.

(3) lipoprotein particles six hours after a standard meal with an increased lipid moiety, which hypothetically masks c, d, f, and g epitopes. This signifies normal absorption and hepatic production of lipoprotein particles as a response to the fatty meal. The epitopes "e" and "h" are unmasked and still available to react with capturing antibody (1). If epitopes e and h are masked by lipids, the capturing of lipoprotein particle does not occur.

(4) lipoprotein particles twelve hours after the fatty meal. The lipid moiety is decreased secondary to lipolysis induced by LPL. As a result of lipolysis, epitopes c–d and f–g are unmasked. (5), (6), and (7) depict three abnormal conditions:

(5) a very small lipid moiety in fast, masking only epitope a. This may be a marker of a severe condition (for example, malignancy) or may be an advantageous situation for lipid transport.

(6) a lipoprotein particle six hours after a standard meal, does not increase the lipid moiety and has the epitopes c–k unmasked like in a fast. This may signify poor absorption of lipids.

(7) Depicts a lipoprotein particle twelve hours after administration of a fatty meal with a large lipid moiety (as in peak absorption time at six hours after a meal), masking c–d and f–g epitopes. This may signify poor LPL activity and subsequent poor lipid clearance.

The pattern of lipid clearance is interpreted with reference to the age of the subject. It is known that the younger the person (under 20), the lower the peak at B, in FIG. 1, and the more rapid the clearance of lipid moieties from the bloodstream (peak occurs at 3 hours, return at 5 hours), and that in older persons (above 76 yrs), the peak is much higher and is reached only at 9 hrs and the clearance takes place in 24 hours after the test meal. The discovery of an adult pattern in a young subject even with normal triglyceride and cholesterol fasting levels will indicate pathology and will predict the development of coronary artery disease.

Schonfeld has suggested a link between specific metabolic functions and critical epitopes of apolipoprotein molecules (Krul, E. and G. Schonfeld, *Methods in Enzymology* 128A:527–553 (1986). Consistent with this, an epitope present on Apo AI stimulates LCAT, while another on Apo AII inhibits LCAT, and the equilibrium depends on the amount of substrate, or lipid moiety loaded onto 1 HDL. It is processes such as these which are detectable according to the procedures of the present invention. There is the possibility, that using this methodology, detection of functional defects in metabolism will permit the application of individualized diet and drug therapy, for epitope modulation and replacement or enzyme modulation (LPL and LCAT) before serum cholesterol becomes elevated and plaque is deposited in vessel walls.

This technology (LMD/EEID) will offer also the tool of studying the variable epitopes and their impact on clinical conditions.

The recommended sequence of studying the samples for LMD/EEID are as follows:

1. Lipid moiety dynamics (LMD).
2. Expressed EPITOPES immunoreactivity dynamics (EEID).
3. Single EPITOPE expressed immunoreactivity dynamics.
4. Variant lipid moiety dynamics (constant number of lipoprotein particles studied).
5. Variant expressed EPITOPES immunoreactivity dynamics (constant number of lipoprotein particles studied).
6. Variant single EPITOPE expressed immunoreactivity dynamics (constant number of lipoprotein particles studied).

Tests 1–3 are quantitative. Tests 4–6 are not quantitative, exploring mainly the size of the particles and performing the epitope scanning.

Tests 1–6 of LMD/EEID can be performed as a panel, individually or in any combination. The number of samples and the time each sample is studied in fast-feeding cycle may vary according with interest.

The lipid challenge is either with a normal meal or a standard meal (for example, 1 gm lipids/kg body).

LMD/EEID OF APO $B_{100}$-CONTAINING LIPOPROTEINS

The suggested protocols are as follows:

EXAMPLE 1

LIPID MOIETY DYNAMICS (LMD)

1. Coating Step: Each 96-well microtitre plate is coated for 16 hours at 4° C. with 0.15 ml of 0.1 mol/L $NaHCO_3$ buffer, pH 9, containing 1 µg of purified mouse monoclonal antibodies raised to non lipid dependent epitopes.

The type of plates used are preferably black plates Microfluor B" (Dynatech Lab, Inc.).

2. Washing Step: The plates are washed×3 with 0.2 ml PBS containing 10 gm gelatin/L. Aspirate dry.

3. Blocking Step: Residual bindings sites are blocked by incubating for one hour at 37° C. with an amount of 0.2 ml of PBS containing 10 gm gelatin/L.

4. Washing Step: Identical with Step 2. Plates prepared in this manner, if stored in humidified chamber can be used up to one month.

5. Capturing Step: The standard and samples are diluted 8,000 fold in PBS and 100 µl are added to each well in triplicate and incubated 2 hours at 37° C.

6. Washing Step: Identical with step 2.

7. Probing Step: Uses Nile Red as a lipid probe.

Suggested preparation of Nile Red solution: Stock solution is prepared dissolving 500–2000 µg Nile Red in 1 ml acetone or ethanol or MOLECUSOL™ cyclodextrines 20% (Pharmatec, Inc., Alachua Fla. 32615). Fresh working solution is prepared mixing 10 µl of stock solution with 1ml MOLECUSOL™ 20% or 1 ml 80/20 methanol/water. From this fresh working solution 100 µl are placed in each well. The staining time should be determined by trial. However, it is expected to be low, under 5 minutes due to high hydrophobicity of the Nile Red.

At low concentrations, 0.166 μg/ml, the Nile Red stains the whole lipid moiety of the lipoprotein. At increasing concentrations (1.66 μg/ml) the Nile Red stains only the amphipathic phospholipids (Greenspan, P. et al., Journal of Lipid Research, 26, 781-9 1985). This "selective" staining should be explored by trial.

8. Washing Step: The staining solution is aspirated and the well washed as in Step 2. Aspirate dry.

9. Reading Step: The fluorescence of each well is read by Fluoroscan II (Flow Laboratories) in red fluorescence (excitation 580 nm, emission 640 nm) or yellow fluorescence (excitation 450 nm–500 nm, emission 528–580 nm). The yellow fluorescence detects predominately neutral lipids. The red fluorescence detects total lipids.

The fluorescence is expressed in absolute fluorescent units or relative fluorescence units and compared to the standard. The reference standards are either CDC lyophilized standard or IUIS standard or other commercial reference standard which can be traced to the above standards (for example from Beckman Instruments, Fullerton, Calif.). A fresh pool of sera can be used as standard as well.

Pre-staining of the standards and sample can be attempted by adding to each, one ml of 8000-fold diluted standard and sample, 5 μl of fresh working solution of Nile Red, agitating the sample for a few seconds, then applying 100 μl of sample as in Step 5; then proceed to steps 8 and 9. This will quantitate LMD in fast-feeding cycle.

EXAMPLE 2

EXPRESSED EPITOPES IMMUNOREACTIVITY DYNAMICS (EEID)

1. Coating Step: Ninety-six-well polystyrene microtitre plates (Nunc Immunoplate I, Irwing Sci., Santa Ana, Calif.) are coated for 16 hours at 4° C. with 150 μl of a 0.1 mol/L $NaHCO_3$ buffer, pH 9, containing 1.0 μg of purified mouse monoclonal antibodies specific to a nonlipid-dependent apo $B_{100}$ epitope.

2. Washing Step: The plates are washed three times with 200 μl PBS containing 10 gm/L BSA. Aspirate dry.

3. Blocking Step: Residual binding sites are blocked by incubating for 1 hour at 37° C. with 200 μl of phosphate buffer saline (PBS) containing 30 gm BSA/l (PBS 0.136 mol of NaCl, 1.46 mmol of $KH_2PO_4$, 8.17 mmol $Na_2HPO_4$ and 2.68 mmol of KCl.L, pH 7.3).

4. Washing Step: After removing the blocking solution, wash the plate×3 with 200 μl PBS containing 10 gm BSA/L. Aspirate dry. Plates prepared in this manner, if stored in a humidified chamber, can be used for up to one month.

5. Capturing Step: The standard is diluted in PBS to yield 3-4 known concentrations which are run under the same conditions as the samples with each series.

The desired assay range is the first parameter to be determined. The controls and samples are diluted 8000-fold in PBS and 100 μl are added to wells in triplicate and incubated 2 hours at 37° C.

6. Washing Step: Identical with step 2.

7. Probing or Scanning Step: One hundred μl of mouse mixture of monoclonals with specificity to immunogenic epitopes of apo $B_{100}$ (or polyclonals with the same specificity) conjugated with horseradish peroxidase, diluted 1/2000 in PBS containing 10 g BSA/L are placed in each well. The plates are incubated 2 hours at 37° C.

8. Washing Step: Identical with step 2.

9. Substrate Addition: One hundred μl of freshly prepared substrate solution (mixture containing 0.05% Ortho-Phenylene-Diamine and 0.05% $H_2O_2$ in phosphate citrate buffer, pH 5) is placed in each well and incubated in the dark for 30 minutes at room temperature.

10. Stopping Color Development: This is performed by adding 50 μl of 4N $H_2SO_4$.

11. Reading Step: Absorbance reading in the individual wells is performed at 490 nm using 96 well automatic plate reader (MR 600; Dynatech, Alexandria, Va.) against blanks. The blanks are run under the same conditions but are incubated without antigen.

When in Step 9 the added substrate is 3-(P-hydroxy phenyl) propionic acid, a fluorescent product develops and the fluorescence is read at 320 nm excitation and 405 nm emission. The reading is performed by Fluoroscan II (Flow Labs) or with a similar device. This will quantitate EEID in plasma samples, in fast-feeding cycles.

EXAMPLE 3

SINGLE EPITOPE EXPRESSED IMMUNOREACTIVITY DYNAMICS

1. Coating Step: Ninety-six well polystyrene microtitre plates are coated for 16 hours at 4° C. with 150 μl of 0.1M $NaHCO_3$ buffer, pH 9, containing 1 μg of purified mouse mixture of monoclonals raised to immunogenic epitopes of apo $B_{100}$ or polyclonal antibodies with the same specificity.

2–6. Steps 2 through 6 are identical with the same steps in Example 2.

7. Probing or Scanning Step: One hundred μl of mouse monoclonal antibodies raised to single studied epitope conjugated with horseradish peroxidase diluted 1/2000 in PBS containing 10 gm BSA/L are placed in each well. The plates are incubated two hours at 37° C.

8–11. Steps 8 through 11 are identical with the same steps in Example 2.

This will quantitate the studied single epitope expressed immunoreactivity dynamics in fast-feeding cycle.

THE VARIANT TEST OF LMD/EEID OF APO $B_{100}$ PARTICLES STUDYING A CONSTANT NUMBER OF LIPOPROTEIN PARTICLES

In order to study a constant number of captured lipoprotein particles, all the antigenic binding sites of coating antibody present in each well should be saturated with lipoprotein particles. This is accomplished by: decreasing the number of antibodies coating each well (Step 1), using nondiluted specimens and increasing the time and temperature in the capturing step (Step 5).

An appropriate working concentration for coating antibodies will be that concentration at which initial one or two serial dilutions of analyte or standard will give the same readings (for example, optical densities).

EXAMPLE 4

VARIANT LIPID MOIETY DYNAMICS (STUDYING A CONSTANT NUMBER OF LIPOPROTEIN PARTICLES)

1. Coating Step: The 96-well microtitre plates are coated for 16 hours a 4° C. with 150 μl of 0.1 mol/L $NaHCO_3$ buffer, pH 9, containing 0.25 μg of purified mouse monoclonal antibody raised to a non-lipid-dependent epitope of apo $B_{100}$.

The preferred plates are black Micro Fluor "B" (Dynatech Lab, Inc.).

2–4. Steps 2, 3 and 4 are identical with similar steps from Example 1.

5. Capturing Step: One hundred μl of nondiluted standard and samples are added to each well in triplicate and incubated 4–6 hours at 37° C.

6–9. Steps 6, 7, 8, and 9 are the same as similar steps in Example 1.

The fluorescence is expressed in absolute or relative fluorescent units per well and compared with standard. A curve may be developed.

This will explores LMD in fast-feeding cycle on a constant number of particles.

EXAMPLE 5

VARIANT EXPRESSED EPITOPES IMMUNOREACTIVITY DYNAMICS (STUDYING A CONSTANT NUMBER OF LIPOPROTEIN PARTICLES)

1. Capturing Step: The 96-well microtitre plates are coated for 16 hours at 4° C. with 150 μl of 0.1 mol/L $NaHCO_3$ buffer, pH 9, containing 0.5–0.25 μg of purified mouse monoclonal antibodies raised to a non-lipid-dependent epitope of apo $B_{100}$.

2–4. Steps 2, 3 and 4 are identical with similar steps in Example 2.

5. Capturing Step: One hundred μl of nondiluted standard and samples are added to each well in triplicate and incubated 4–6 hours at 37° C.

6–11. Steps 6, 7, 8, 9, 10 and 11 are identical with similar steps from Example 2.

The readings obtained in standards and samples are compared and expressed in optical densities per well. This will estimate EEID in plasma samples in fast-feeding cycle (compared with a standard) on a fixed number of lipoprotein particles. A curve may be developed.

EXAMPLE 6

VARIANT SINGLE EPITOPE EXPRESSED IMMUNOREACTIVITY DYNAMICS (STUDYING A CONSTANT NUMBER OF PARTICLES)

1. The 96-well microtitre plates are coated for 16 hours at 4° C. with 150 μl of 0.1 mol/L $NaHCO_3$ buffer, pH 9, containing 0.5–0.25 μg mouse mixture of monoclonals raised to immunogenic epitopes of apo $B_{100}$ (or polyclonals with the same specificity).

2–4. Steps 2, 3 and 4 are identical with similar steps in Example 2.

5. Capturing Step: One hundred μl of nondiluted standard and samples are added to each well in triplicate and incubated 4 to 6 hours at 37° C.

6. Step 6 is identical with the same step in Example 2.

7. Probing or Scanning Step: One hundred μl of mouse monoclonal antibodies raised to a single studied epitope conjugated with horseradish peroxidase diluted 1/2000 in PBS containing 10 gm BSA/L are placed in each well. The plates are incubated 2 hours at 37° C.

8–11. Steps 8, 9, 10 and 11 are identical with the same steps in Example 2.

The readings obtained in standard and samples are compared and expressed in OD/well. This will explore the studied epitope expressed immunoreactivity in fast-feeding cycle of a constant number of particles. A curve maybe developed.

EPITOPE SCANNING OF PROTEIN MOLECULES OTHER THAN LIPOPROTEINS

EXAMPLE 7

EPITOPE SCANNING OF HUMAN LIPOPROTEIN LIPASE (LPL)

1. Coating Step: Ninety-six well microtitre plates are coated for 16 hours at 4° C. with 150 μl of 0.1 mol/L $NaHCO_3$ buffer, pH 9, containing 0.5–0.25 μg of purified mouse monoclonal antibodies raised to a known epitope of LPL molecule.

2–4. Steps 2, 3 and 4 are identical with similar steps in Example 2.

5. Capturing Step: One hundred μl of post-Heparin plasma undiluted is added to each well in triplicate and incubated 4–6 hours at 37° C. (or 72 hours at 4° C.) the standard is a pool of plasma obtained in the same manner from healthy adults (between 18–20 years of age).

6. Washing Step: The plates are washed three times with 200 μl PBS containing 10 gm/L BSA. Aspirate dry.

7. Probing or Scanning Step: In each well is added 100 μl of a fixed concentration of a mixture of mouse monoclonal antibodies raised to immunogenic epitopes of LPL (or polyclonal antibodies with same specificity) conjugates with horseradish peroxidase diluted 1/2000 in PBS, containing 10 gm BSA/L. The plates are incubated 6 hours at 37° C. or 72 hours at 4° C.

8–11. Steps 8, 9, 10 and 11 are the same as identical steps in example 2.

Any difference in absorbance readings between analyte and standard will indicte a difference between the epitopes from analyte molecule and epitopes from standard molecule; therefore, indicating an abnormal molecule.

The same absorbance reading will indicate no differences in epitope composition between analyte molecule and standard molecule. If probing antibody conjugated with peroxidase in Step 7 is a monoclonal with specificity for a known LPL epitope, the presence of this specific epitope on molecule is scanned and compared with the standard.

EXAMPLE 8

KITS FOR USE IN PERFORMING LMD/EEID TESTS

Specific test kits are constructed for detecting lipid moieties and expressed epitope immunoreactivity and their dynamics using techniques for visualization and measurement.

1. One test kit for LMD determinations comprises a compartmented enclosure containing ready-to-use black plates with multiple wells coated with capturing antiboides specific for a selected apolipoprotein, together with other materials such as containers with reagents for fresh preparation of blocking gelatin solution (PBS with 10 g/l gelatin), washing solution (PBS with 10 g/l gelatin) and staining Nile Red.

2. Another test kit for variant LMD, studying a constant number of lipoprotein particles, comprises a compartmented enclosure containing, ready for use, black plates with multiple wells coated with appropriate amount and type of capturing antibodies specific for a selected apolipoprotein and some additional materials as in the test kit for LMD determination.

3. A different test kit for EEID determinations, comprises a compartmented enclosure containing ready for use plates, coated with capturing antiboides specific for a selected apolipoprotein, together with peroxidase-labelled probing antibodies, with precisely known specificity and containers with reagents for fresh preparation of blocking albumin solution (PBS with 30 g/L BSA), washing solution (PBS with 10 g/L BSA), substrate (ortho-phenylene-Diamine and 0.05% hydrogen peroxide in phosphate citrate buffer) and stopping solution (4N $H_2SO_4$).

4. Another test kit for variant EEID determination, studying a constant number of lipoprotein particles, comprises of a compartmented enclosure containing plates with multiple well coated with appropriate amount and type of capturing antibodies specific for a selected apolipoprotein, together with same additional materials as in the test kit for EEID determination.

All kits further contain a specimen of CDC or IUIS lipoprotein standard human serum.

NOVELTY AND ADVANTAGES

The test methodology made available by this invention comprises the first methodology of quantifying both lipid moiety and expressed epitope immunoreactivity in intact lipoprotein particles. Testing the dynamics of lipid moiety and expressed epitope immunoreactivity after a stress fatty meal in apo $B_{100}$ and apo $A_1$-containing lipoprotein particles, explores the very reason for existence of lipoproteins, the transport of lipids. All previous methods of testing are done only in the fasting state.

The development of LMD/EEID is based upon the idea of mutual interaction between lipids and apolipoprotein moieties in intact lipoprotein particles. LMD/EEID can be performed in any class of lipoprotein particles, being limited only by the ability to generate a specific capturing antibody for a specific class of lipoprotein particles. The test offers the possibility of simultaneous evaluation of events occurring at the same time in different lipoprotein particles. The panel can be expanded from apo $B_{100}$ and apo $A_1$-containing particles to all other apolipoprotein particles (Lp(a), oxidized LDL, etc.).

This is the first clinical test exploring simultaneously the normal anatomy (lipid moiety, expressed immunoreactivity) and function of intact lipoprotein particles (lipid absorption, postprandial lipolysis, nocturnal lipolysis, epitope dynamics). It also combines in a unique clinical test the fatty meal, the intact lipoprotein particle, and the dynamics of lipid moiety and expressed epitope immunoreactivity, using the same technology (for example, ELISA). The marker for coronary artery disease is no longer lipid moiety (cholesterol or apolipoprotein). The marker is abnormal lipid moiety dynamics/expressed epitope immunoreactivity dynamics (LMD/EEID). This offers the possibility of detecting the abnormality earlier and before the cholesterol is elevated. The test will offer an individualized indication for diet and drug therapy, for epitope modulation or replacement or enzyme modulation and replacement (LPL, LCAT).

This invention permits a noninvasive study of lipid metabolism, a dissection at the molecular and submolecular level of events and structures with therapeutic consequences and a better understanding of the lipid metabolism. It opens an immense field of research, a revolution in studying lipoproteins, atherosclerosis, and risk for coronary artery disease. Moving from quantification of parts, isolated components of lipoprotein particles (lipid fractions or apolipoprotein moieties) to the whole lipid moiety or expressed epitope immunoreactivity (not artificially delipidated apolipoproteins) in an intact lipoprotein particle, represents a dramatic progress.

At the same time, moving from quantification in single samples (a static approach) to multiple samples in fast and after meals (a dynamic approach) is another definite progress. I suggest that the time has come to replace the quantification of total cholesterol, HDL cholesterol, LDL cholesterol, and triglyceride with that of the lipid moiety, which incorporates all these fractions in fast and dynamics after a meal or meals.

I also suggest that the time has come to change our approach from quantifying the immunoreactivity of certain apolipoproteins in fast only (a static approach) to quantifying the expressed epitopes or epitope immunoreactivity in fast and after a meal (a dynamic approach).

The method can be used to identify the effects of drugs and toxics on lipoproteins and other proteins before and after treatment or exposure.

This new approach will generate a multitude of meaningful physiological and physiopathological information about apolipoprotein $A_1$ and apolipoprotein $B_{100}$-containing lipoprotein particles, or any other lipoproteins, such as:

1. The absorption of lipids
2. The efficiency of lipolysis
3. An indirect evaluation of lipoprotein lipase complex activity
4. The function of different expressed epitopes, variable and stable, on apolipoprotein molecules incorporated in normal anatomy of lipoprotein particles.

This methodology can be applied to any lipoprotein particle. This new way of testing will stimulate a great interest for the industry:

1. To develop selective lipid probes for cholesterol esters, cholesterol, triglyceride, phospholipids, and the like.
2. To scan the epitopes on apolipoprotein molecules incorporated in lipoprotein particles, to isolate and synthesize functional epitopes for replacement therapy and diagnostic purposes.
3. To devise, synthesize, stimulating epitopes for different key enzymes such as LPL and LCAT. This will lead to the ability to modulate the LPL activity (enhancing or blocking) using isolated synthesized epitopes as well as a new pharmacological approach.
4. To modulate apolipoprotein activity synthesizing functionally active epitopes, peptides, inhibitory or stimulating epitopes of certain enzymes (such as LPL or LCAT) in order to replace the nonfunctional ones detected by the test.
5. To develop artificially prepared lipoprotein particles incorporating the missing or malfunctioning epitopes in view of replacement therapy.
6. To develop epitope specific monoclonals for testing.
7. To develop dedicated photometers, fluorometers, and luminometers able to generate printouts with curves of LMD/EEID and interpretation of results.

It should be emphasized that the present invention is not limited to the use of any particular analytical methodology; rather, the beneficial results of the present invention flow from the simultaneous or sequential determination of lipid moieties and expressed epitope immunoreactivity on apolipoprotein in the same intact, native lipoproteins. The determinations can be made periodically throughout the fast-feeding cycle, or at any selected point in this cycle. Thus, regardless of a particular analytical methodology for these determinations is presently known, or whether it becomes known in the future, the methods of performing the presently-contemplated determinations therefrom are based on established techniques, as will be apparent to those of skill in the art, and their incorporation into the LMD/EEID analysis is broadly enabled by the preceding disclosure. It should be emphasized again that the present techniques are broadly applicable to a variety of analytical formats for use in the practice of the present invention.

Accordingly, the invention may be embodied in other specific forms without departing from it spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced with their scope.

What is claimed is:

1. A method for detecting abnormal epitope expression on a preselected protein present in a test sample of biological fluid from normal epitope expression on the preselected protein present in a reference sample of the biological fluid, wherein said preselected protein comprises at least two non-overlapping epitopes, comprising;

(a) providing an undiluted aliquot of the test sample;
  (b) providing an undiluted aliquot of the reference sample, wherein the reference sample comprises a pool of the biological fluid obtained from a control population of healthy adults;
  (c) immunocapturing a predetermined constant number of molecules of the preselected protein from the undiluted aliquots of the test and reference samples by
    (1) providing a solid phase comprising a test area and a reference area, wherein
      (i) each area comprises an immobilized capture antibody which specifically binds to one of the at least two non-overlapping epitopes, and
      (ii) the capture antibody in each area is present in a saturable, limited amount sufficient to capture the predetermined constant number of molecules of the preselected protein from the undiluted aliquots of the test and reference samples, but in an amount insufficient to capture all of the molecules of the preselected protein in the undiluted aliquots of the test and reference samples;
    (2) contacting the test and reference areas with the aliquots of undiluted test and reference samples, respectively, at a temperature and for a period of time sufficient to completely saturate all available binding sites on the immobilized capture antibody with the preselected protein; and
    (3) removing any unbound molecules of the preselected protein from the test and reference areas;
  (d) contacting the captured predetermined constant number of molecules of the preselected protein in the test and reference areas of step (c) with a predetermined excess amount of a probe comprising a label and an antibody which specifically binds to the other of the at least two non-overlapping epitopes;
  (e) measuring the amount of the label bound to the solid phase of step (d) in each of the test and reference areas; and
  (f) comparing the measured amount of the label bound in the test area to the measured amount of the label bound in the reference area, wherein any difference between the measured amounts indicates abnormal epitope expression on the preselected protein present in the test sample from normal epitope expression.

2. The method defined in claim 1, step (e), wherein the label is an enzyme and the measuring of the bound label is carried out by colorimetric means, fluorometric means, or luminescent means.

3. The method defined in claim 1, step (e), wherein the label is a fluorescent substance and the measuring of the bound label is carried out by fluorometric means.

4. The method defined in claim 1, step (e), wherein the label is a radioactive isotope and the measuring of the bound label is carried out by radiometric means.

* * * * *